United States Patent [19]

Convers et al.

[11] 4,087,474
[45] May 2, 1978

[54] PROCESS FOR THE PURIFICATION OF 1,2-DICHLOROETHANE

[75] Inventors: Ronald J. Convers, Ponca City, Okla.; Paul L. Fetzer; Homer L. Hackett, both of Lake Charles, La.; Charles M. Starks, Ponca City, Okla.

[73] Assignee: Continental Oil Company, Ponca City, Okla.

[21] Appl. No.: 804,113

[22] Filed: Jun. 6, 1977

[51] Int. Cl.² ............................................. C07C 17/38
[52] U.S. Cl. ................................. 260/652 P; 568/867
[58] Field of Search ..................................... 260/652 P

[56] References Cited

U.S. PATENT DOCUMENTS

| | | | |
|---|---|---|---|
| 2,799,716 | 7/1957 | Brummet | 260/652 P |
| 3,378,597 | 4/1968 | Dehn et al. | 260/652 P |
| 3,691,239 | 9/1972 | Hackett et al. | 260/652 P |
| 3,996,300 | 12/1976 | Ahlstrom | 260/652 P |
| 4,028,427 | 6/1977 | Tsao | 260/652 P |

FOREIGN PATENT DOCUMENTS

| | | | |
|---|---|---|---|
| 50-16,766 | 1975 | Japan | 260/652 P |

*Primary Examiner*—Joseph E. Evans
*Attorney, Agent, or Firm*—Cortlan R. Schupbach

[57] ABSTRACT

A method for the disposal of 2-chloroethanol by conversion to readily biodegradable ethylene glycol comprising;

(1) extracting 2-chloroethanol into a neutral or acidic aqueous solution;
(2) adjusting the pH of the solution to at least 10 and heating to a temperature of from about 25° C to about 100° C to form ethylene oxide and ethylene glycol,
(3) stripping the basic solution of (2) to obtain a basic aqueous phase and a distillate, the basic aqueous phase being disposed, and
(4) condensing and hydrolyzing the distillate and
(5) stripping said hydrolysate, recovering the volatile organic portion, and
(6) disposing of ethylene glycol in aqueous solution.

3 Claims, No Drawings

PROCESS FOR THE PURIFICATION OF 1,2-DICHLOROETHANE

This invention deals with a method for the disposal of 2-chloroethanol by conversion to readily biodegradable ethylene glycol. More particularly this invention deals with a method for the disposal of 2-chloroethanol from industrial 1,2-dichloroethane (EDC) solutions into a readily biodegradable, environmentally acceptable form such as ethylene glycol.

During the production of 1,2-dichloroethane (EDC), 2-chloroethanol is formed as a by-product. While 2-chloroethanol is only a minor by-product of commercial ethylene oxychlorination processes, this material is very troublesome to plant operations for many reasons. The by-product, 2-chloroethanol, is water soluble and toxic at low concentrations to conventional plant bio-pond microorganisms which purify effluent streams. Plant effluents with excessive oxygen demand and particulate matter can thus result from 2-chloroethanol production, since bio-pond microorganisms are destroyed by contact with 2-chloroethanol. The 2-chloroethanol is a precursor to oxygenates such as ethylene oxide (EO) and acetaldehyde produced from base treatment or thermal cracking. These oxygenates presently decrease the market value of the low boiling by-product chlorohydrocarbon streams known in the industry as EDC light ends. In addition, 2-chloroethanol is believed to be responsible for corrosion of steel in distillation towers used to recover EDC light ends, because of thermal cracking to hydrochloric acid and ethylene oxide and acetaldehyde. Further, 2-chloroethanol is believed to cause excessive tar formation during production of vinyl chloride by the thermal cracking of EDC.

Thus it is very apparent that it is desirable to remove 2-chloroethanol from commercial ethylene oxychlorination product streams. Commercial plants presently depend on aqueous sodium hydroxide washes of crude EDC to convert 2-chloroethanol to less troublesome derivitives such as ethylene oxide or ethylene glycol.

However, during present attempts to convert 2-chloroethanol to ethylene oxide followed by the hydrolysis of ethylene oxide to ethylene glycol in conventional plant systems, it has been found that 2-chloroethanol is ultimately not removed completely but instead continues to pass to the bio-pond where its harmful effects previously described continue to be felt.

The reaction to form ethylene oxide is rapid even in the usual 2-phase wash system commonly used in commercial facilities in the present art. However, the sodium hydroxide conversion of 2-chloroethanol to the desirable ethylene glycol is so slow as to be commercially impractical using conventional 2-phase wash systems; and the ethylene oxide reconverts to 2-chloroethanol in the presence of HCl, traces of which are found in later parts of the EDC purification train.

It is known in the art that ethylene oxide can be hydrolyzed to form ethylene glycol and that 2-chloroethanol can be converted to ethylene oxide. While such references are too numerous to mention, representative examples can be found in U.S. Pat. No. 2,839,588; U.S. Pat. No. 2,742,505; Stanford Institute Research Reports No. 70 and 70A, Journal of American Chemical Society Volume 80, pages 4162 through 4165, and Hydrocarbon Processing, Volume 46, issue four, pages 176 through 178, 1967.

It would therefore be greatly desirable to devise a process whereby 2-chloroethanol can be economically, quickly and completely removed from crude EDC streams and converted into relatively harmless ethylene glycol for bio-pond disposal.

It is therefore an object of the present invention to provide a method for the removal of 2-chloroethanol from commercial EDC streams by the formation of ethylene glycol which is readily biodegradable. Other objects will become apparent to those skilled in this art as the description proceeds.

It has now been discovered according to the instant invention that 2-chloroethanol can be removed from EDC streams by conversion to readily biodegradable ethylene glycol using a process which comprises, (1) extracting 2-chloroethanol into an acidic or neutral aqueous solution,
(2) adjusting the pH of the solution of (1) to a basicity of at least 10 and heating to a temperature of from about 25° to about 100° C to form ethylene oxide and ethylene glycol,
(3) stripping the basic solution of (2) to obtain a basic aqueous phase and a distillate, the basic aqueous phase being disposed and,
(4) condensing and hydrolyzing the distillate and,
(5) stripping the hydrolysate, recovering the volatile organic portion and,
(6) disposing of ethylene glycol in aqueous solution.

Preferred temperature ranges of (2) are from about 45° to about 75° C. Lower temperatures in this are preferred in order to avoid decomposition of product EDC.

The process described in the instant invention requires that the crude EDC to be purified is extracted with that volume or number of stages of aqueous solution, preferably water, which will reduce the 2-chloroethanol concentration in EDC to the optimum level, defined as that level consistent with a favorable economic balance of water and equipment costs compared to costs associated with usual 2-chloroethanol concentrations in EDC. For example, the partition coefficient of 2-chloroethanol between EDC and water is about 0.28. This means that 2 successive water washes of crude EDC in a 1:1 weight to weight ratio can remove about 95% of the original 2-chloroethanol from the EDC. Water extraction systems are of course well-known industrially.

The washed EDC is then suitable for reinjection into conventional purification trains. The combined aqueous extracts are then treated with sufficient sodium hydroxide or other suitable base to maintain a pH equal or greater to 10 and most preferably adjusted to a temperature of from about 50°–60° C to rapidly convert the 2-chloroethanol, mainly to ethylene oxide and a smaller amount of ethylene glycol. It is also known that the sodium hydroxide conversion of 2-chloroethanol to ethylene oxide in warm aqueous solution is rapid.

It has been unexpectedly discovered that the basic aqueous solution which usually contains NaCl, $Na_2CO_3$, sodium formate, sodium hydroxide, water, EDC, ethylene oxide, ethylene glycol, and chloroform, must be steam or azeotropically stripped to separate ethylene oxide, EDC, and chloroform (chloroform formed from the base decomposition of chloral, another EDC by-product) from the salt solution. This step is critical since the invention procedure is unpredictably inoperative without such a separation. The aqueous phase resulting from the steam stripping is then free of 2-chloroethanol and EDC and ready for disposal, such as in a bio-pond. This stripping of the aqueous phase is especially useful since EDC is also known as a bio-pond toxin and is removed in the organic phase.

The stripped organic phase and some water are condensed, and the ethylene oxide is hydrolyzed in the presence of a hydration catalyst such as strong acids, acidic salts, or other catalysts known in the ethylene oxide hydration art. It is well known that the sulfuric acid catalyzed hydration of warm dilute aqueous ethylene oxide is rapid. Thus for economy, sulfuric acid is a preferred catalyst.

The hydrolysate is then steam stripped. The stripped organics are reinjected into the conventional purification train. The aqueous solution of ethylene glycol is now free of 2-chloroethanol and EDC and is preferably combined with the previously stripped aqueous base stream before disposal through conventional bio-ponds.

The entire product of a two phase water and EDC base wash system could be steam stripped for the purpose of the instant invention. However, excessive energy and equipment size costs would result from attempts to steam strip an entire commercial oxychlorination EDC stream. The instant invention provides concentration of the undesirable material using the prior art water extraction step to give a stream more easily steam stripped. Since the EDC (main product of the oxychlorination) has only about a 2 percent solubility in water, the bulk of organics to be steam stripped is greatly reduced.

The invention is more concretely described with reference to the examples below wherein all parts and percentages are by weight unless otherwise specified. The examples are provided to illustrate the present invention and not to limit it.

Examples 1 and 2 show that the base conversion of 2-chloroethanol to ethylene oxide is very dependent upon pH, a pH of greater or equal to 10 being required for practical reaction rates. Examples 3, 4, and 5 show that ethylene oxide in the presence of sodium chloride and strong, non-halogen acid such as sulfuric acid readily produces 2-chloroethanol, showing that ethylene oxide formed during the base treatment step must be separated from concurrently formed NaCl to prevent reconversion to undesirable 2-chloroethanol. These examples also illustrate the existence of a ethylene oxide/sodium chloride reaction. In addition, the magnitude of this reaction is extremely surprising. Examples 6 and 7 show that 2-chloroethanol is not formed during the two phase hydration of ethylene oxide in the absence of sodium chloride.

EXAMPLE 1

A mixture of 78.5 grams (g) of an EDC solution containing 0.35 weight percent of 2-chloroethanol, and 0.98 weight percent chloral hydrate and 19 g of a 3.0 weight percent aqueous $Na_2CO_3$ solution was stirred magnetically at 58°–60° C in a 100 ml Morton flask with a dry ice-acetone condenser. After 2 hours, gas liquid chromatographic (GLC) examination showed about 40% of the original 2-chloroethanol remaining in the EDC phase and about 14% of the 2-chloroethanol present in the aqueous phase using external standard comparisons. The final aqueous pH was 8. The GLC used was a 10 ft by ⅛ inch stainless steel column, 7.6 weight percent FFAP on 100–115 mesh Chromosorb HP (trademark of and sold by Johns-Manville), a commercial solid support for the liquid phase (FFAP) about 112° C, using a flame ionization detector (FID).

EXAMPLE 2

The procedure of Example 1 was repeated except that an aqueous 3.0 weight percent sodium hydroxide solution was used instead of the sodium carbonate solution. The final aqueous pH was 10. GLC showed no 2-chloroethanol remaining in EDC phase after 10 minutes.

EXAMPLE 3

A 10 weight percent solution of ethylene oxide in EDC was prepared and designated solution A. A solution containing 0.57 g of sodium carbonate, 0.46 g of sodium formate, 0.18 g of sodium hydroxide, and 1.40 g of sodium chloride in 18.9 g of water was prepared and designated solution B.

A mixture of 7.64 g of solution A, 2.11 g of solution B, and 0.23 g of 98% sulfuric acid was shaken at ambient temperature for about two minutes in a capped 2 ounce glass bottle. GLC examination of the EDC phase showed most of the ethylene oxide remaining and 0.22 weight percent 2-chloroethanol present. GLC showed 0.04 weight percent 2-chloroethanol present in A in duplicate runs. After periodic shaking over about 1.5 hours at ambient temperature the sulfuric acid washed EDC phase contained about 0.2 weight percent ethylene oxide and 0.7 weight percent 2-chloroethanol. The aqueous phase after about 3 hours contained essentially only EDC and 1.4 weight percent 2-chloroethanol.

EXAMPLE 4

A mixture of 7.64 g of a 0.20 weight percent ethylene oxide solution in EDC, 2.11 g of solution B as shown in Example 3, and 0.23 g of 98% sulfuric acid was shaken at ambient temperature in a 2 ounce glass bottle over about 2 minutes. GLC showed about ⅓ of the ethylene oxide remaining and 0.07 weight percent 2-chloroethanol present in the EDC phase. GLC showed no measurable 2-chloroethanol in the starting ethylene oxide solution. After 2 hours at ambient temperature with periodic shaking, the EDC phase contained about 2% of the original ethylene oxide and 0.10 weight percent 2-chloroethanol.

EXAMPLE 5

A mixture of 7.64 g of solution A as prepared in Example 3, 1.9 g of water, 0.14 g of NaCl, and 0.23 g of 98% sulfuric acid was shaken at ambient temperature over about 2 minutes in a 2 ounce glass bottle. GLC examination of the EDC phase showed 1.4 weight percent 2-chloroethanol present.

EXAMPLE 6

A mixture of 7.64 g of solution A prepared as described in Example 3, 1.9 g of water, and 0.23 g of 98% sulfuric acid was shaken at ambient temperature for about 2 minutes in a capped 2 ounce glass bottle. GLC showed most of the ethylene oxide remaining and only 0.06 weight percent 2-chloroethanol present in the EDC. GLC showed little change after the mixture stood at ambient temperature for 15 minutes.

EXAMPLE 7

A mixture of 7.64 g of solution A prepared as described in Example 3, 1.9 g of water, and 0.23 g of sulfuric acid was shaken at about 50° C for about 2 minutes in a capped 2 ounce glass bottle. GLC showed no ethylene oxide remaining and less than 0.01 weight percent 2-chloroethanol present in the EDC phase. The starting ethylene oxide solution contained 0.06 weight percent 2-chloroethanol. The aqueous phase contained about 70% of this starting 2-chloroethanol after the hydrolysis reaction.

An examination of the instant invention in comparison to the prior art will reveal that the present invention has provided a method for the removal of 2-chloroethanol from commercial EDC streams by a process of concentrating the troublesome material into a relatively strong stream, converting to ethylene oxide in a basic aqueous phase, removing the ethylene oxide from the phase using steam stripping and hydrolyzing the ethylene oxide to ethylene glycol while recovering desirable organics. The invention avoids the problems found in the prior art, i.e. when using known reactions, 2-chloroethanol remained in streams going to bio-ponds. In the process of the instant invention, 2-chloroethanol in effluent streams is reduced to acceptable levels and the majority of the 2-chloroethanol is first converted to ethylene oxide then hydrolyzed to ethylene glycol, which is readily biodegradable.

While certain embodiments and details have been shown for the purpose of illustrating this invention, it will be apparent to those skilled in this art that various changes and modifications may be made herein without departing from the spirit or the scope of the invention.

We claim:
1. A method for purifying an ethylene oxychlorination product stream comprising;
   (1) extracting said stream with a neutral or acidic aqueous solution to obtain a washed 1,2-dichloroethane stream, and an aqueous extract comprising 2-chloroethanol;
   (2) adjusting the pH of said aqueous extract to at least 10 and adjusting the temperature to a range of from about 25° to about 100° C to convert 2-chloroethanol to ethylene oxide and ethyleneglycol;
   (3) stripping the basic solution of (2) to obtain an aqueous phase, said aqueous phase being discarded, and a distillate comprising ethylene oxide, ethylene dichloride and chloroform;
   (4) condensing and hydrolyzing the distillate to convert ethylene oxide to ethylene glycol; and
   (5) stripping the hydrolysate to obtain an aqueous solution of ethylene glycol which is discarded, and an overhead comprising ethylene dichloride and chloroform, which overhead is combined with the washed 1,2-dichloroethane stream.

2. A method as described in claim 1 wherein the temperature of (2) is from about 45° to about 75° C.

3. A method as described in claim 1 wherein the combined overhead and washed 1,2-dichloroethane is distilled to obtain purified 1,2-dichloroethane.

* * * * *